United States Patent [19]

Miller et al.

[11] Patent Number: 5,428,161
[45] Date of Patent: Jun. 27, 1995

[54] PHENAZINE DYES

[75] Inventors: Alan G. Miller; Balchunis: Robert J., both of St. Paul, Minn.

[73] Assignee: Minnesota Mining and Manufacturing Company, Saint Paul, Minn.

[21] Appl. No.: 628,943

[22] Filed: Dec. 14, 1990

Related U.S. Application Data

[63] Continuation of Ser. No. 456,591, Jan. 2, 1990, abandoned, which is a continuation of Ser. No. 185,692, Apr. 26, 1988, abandoned, which is a continuation-in-part of Ser. No. 656,586, Oct. 1, 1984, abandoned.

[30] Foreign Application Priority Data

Oct. 7, 1985 [EP] European Pat. Off. ........... 85905257
Jun. 5, 1987 [WO] WIPO ................. PCT/US85/01920

[51] Int. Cl.⁶ .................. C07D 241/46; C07D 241/42; C07D 471/04; C07D 413/10
[52] U.S. Cl. .................................. 544/115; 544/343; 544/348
[58] Field of Search ............................ 544/348, 115

[56] References Cited

U.S. PATENT DOCUMENTS

| | | | |
|---|---|---|---|
| 3,951,974 | 4/1976 | Crabtree | 260/249.5 |
| 3,972,879 | 8/1976 | Psaar | 260/267 |
| 3,992,381 | 11/1976 | Crabtree | 260/256.5 |
| 4,012,378 | 3/1977 | Crabtree | 260/240 |
| 4,237,281 | 12/1980 | Long | 544/99 |
| 4,380,666 | 4/1983 | Gabrielsen et al. | 564/82 |
| 4,753,890 | 6/1988 | Smith-Lewis | 436/74 |

FOREIGN PATENT DOCUMENTS

| | | |
|---|---|---|
| 0124296 | 11/1984 | European Pat. Off. . |
| 2249133 | 5/1975 | France . |
| 2154659 | 7/1976 | Germany . |
| 2758036 | 7/1979 | Germany . |
| 1416990 | 12/1975 | United Kingdom . |
| WOA8702048 | 4/1987 | WIPO . |

OTHER PUBLICATIONS

Chapman, "Correlation Analysis in Chemistry" (1978), pp. 439–481.
Large's Handbook of Chemistry, 12th Edition, pp. 3–132 to 3–137 (1964).
Hackh's Chemical Dictionary, p. 14 (1960).
Hine, "Physical Organic Chemistry", 2nd Ed. (1962) p. 87.
Carey, "Advanced Organic Chemistry, Part A", 2nd Edition (1986) p. 183.
Sauer, T. Amer. Chem. Soc. 59, 96–103 (1937).
Chemical Reviews 17, 125–136 (1935).
Munch, "Advanced Organic Chemistry", 3rd Ed. pp. 242–250 (1985).
Charton, J. Org. Chem 28, 3131 (1963).
Large's Handbook of Chemistry, 12th Ed. pp. 3–132 to 3–137 (1970).
Chapman, "Correlation Analysis in Chemistry" (1978) pp. 439–481.
Cain Chemical Abstracts article No. 70:95108g vol. 70, 1969.
Chemical Abstracts article No. 86:157045s, vol. 86, 1977.
Chemical Abstracts article No. 4709p, vol. 74, 1971.
Endo Chemical Abstracts article No. 64:1228e, vol. 64, 1965.
Vendetti Chemical Abstracts article No. 61:11208y vol. 61, 1964.

*Primary Examiner*—Mark L. Berch
*Attorney, Agent, or Firm*—Gary L. Griswold; Walter N. Kirn; David L. Weinstein

[57] ABSTRACT

3,7-Diamo phenazine dye having at least one electron-withdrawing substituent on at least one of the groups attached to the amine groups at the 3- and 7-positions, provided that the algebraic sum of the para position Hammett sigma ($p_p$) values for the groups attached to the nitrogen atoms of the amine groups at the 3- and 7-positions is more positive khan about −0.6. The group containing the electron-withdrawing substituent can be selected from
(1) a substituted alkyl group, and
(2) a substituted aryl group.

5 Claims, No Drawings

PHENAZINE DYES

CROSS-REFERENCE TO RELATED APPLICATION

This is a continuation of application Ser. No. 07/1185,692 filed Apr. 26, 1988, which is a continuation-in-part of application Ser. No. 06/656,586, filed Oct. 1, 1984.

BACKGROUND OF THE INVENTION

This invention relates to phenazine dyes, and more particularly, to phenazine dyes suitable as intermediates for leuco phenazine dyes.

Phenazine dyes have been used for many industrial purposes for over 100 years. Well known examples of phenazine dyes include Heliotrope B, and phenosafranine. Essentially all of the phenazine dyes capable of providing red, orange, and magenta hues have unsubstituted amine groups at the 3- or 7-position, or both.

The presence of unsubstituted amine groups at the 3- or 7-positions, or both, does not allow one to employ a simple, direct method to reduce and acylate the dye at the 10-position without also acylating the dye at the 3- or 7-position or both. In a reduced leuco dye which contains acyl groups at the 10-position as well as the 3- and/or 7-positions, reoxidation under normal conditions removes only the acyl group at the 10-position, which will yield a dye form having different absorption properties from that of the original, unreduced dye containing the unsubstituted amine group. Therefore, phenazine dyes known in the art, such as phenosafranine, which are red, magenta, and the like, do not provide the original dye color upon reduction, acylation and reoxidation. In addition, a phenazine dye acylated at the 10-position and containing a free amine group at the 3 and/or 7-positions provides a very unstable leuco dye form in an imaging system containing a metal nitrate, due to the presence of the unsubstituted amine group. Thus, there is no known method for providing phenazine dyes which can be converted to stable leuco forms and then reoxidized to give orange, red and magenta colors in a metal nitrate system. Although phenazine dyes containing substituents at the 3- and 7-positions are well known, essentially all of them provide turquoise or blue colors.

British Patent Specifications 1,443,403 and 1,440,948 describe phenazine dyes for use on cellulosic and other fibers having substituents on the 3- and 7-positions. These substituents are sulfonated phenyl and sulfonated benzyl groups. Although these sulfonated groups provide enhanced water solubility of the dye, they cannot be converted to stable leuco forms that can be oxidized to form orange, red, or magenta colors. British Patent Specification 1,193,923 describes phenazine dyes having long chain alkyl groups attached to the aromatic rings thereof. Although long alkyl chains reduce the mobility of and diffusibility of the dyes, they impart a high molecular weight and low solubility, and they cannot be converted to stable leuco forms that can be oxidized to form orange, red, or magenta colors.

SUMMARY OF THE INVENTION

This invention involves 3,7-diamino phenazine dyes wherein the algebraic sum of the para position Hammett sigma ($\rho_p$) values for the groups attached to the nitrogen atoms of the amine groups at the 3- and 7- positions is more positive than about $-0.52$. This is accomplished by substituting at least one of the groups attached to the nitrogen atoms at the 3- and 7- position with an electron-withdrawing group.

These dyes can be used to prepare reduced leuco dyes that are capable of being oxidized to provide red, yellow, magenta, and orange colors. The dyes in their leuco form can be made to possess sufficient stability to avoid premature oxidation in imaging systems. The oxidized form of the phenazine dyes have good stability to heat and light.

DETAILED DESCRIPTION

The phenazine dyes of the present invention can be represented by the resonant structures:

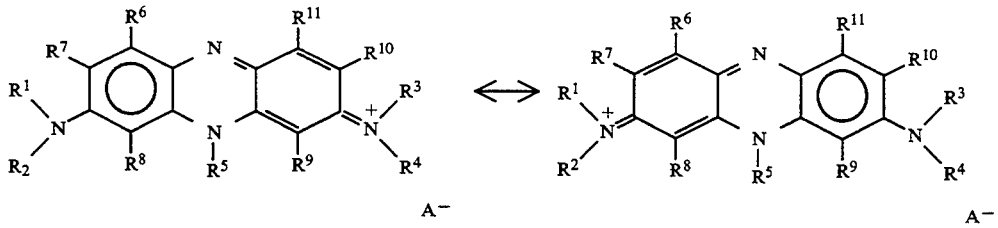

wherein $R^1$, $R^2$, $R^3$, $R^4$ independently represent members of the group selected from unsubstituted alkyl groups, substituted alkyl groups, unsubstituted acyl groups, substituted acyl groups, unsubstituted aryl groups, substituted aryl groups, and hydrogen, provided that the sum of the Hammett substituent constants for $R^1$, $R^2$, $R^3$, and $R^4$, is equal to or greater than about $-0.52$;

$R^5$ represents a member of the group selected from unsubstituted alkyl groups, substituted alkyl groups, unsubstituted aryl groups, and substituted aryl groups;

$R^6$, $R^7$, $R^8$, $R^9$, $R^{10}$, and $R^{11}$ independently represent members of the group selected from hydrogen, halogens, unsubstituted alkyl groups, substituted alkyl groups, unsubstituted alkoxy groups, and substituted alkoxy groups; and $A^-$ represents any stable anion, e.g., $Cl^-$, $I^-$.

As used herein, the term stable anion means any anion capable of existing in solution with the dye without reacting with it in any way that would affect its functioning as a dye.

The colors exhibited by the dyes of the present invention may be determined by standard spectrophotometric techniques, wherein light absorption is plotted as a function of the wavelength of the incident light, from which plot the wavelength of maximum absorption, i.e. $\lambda$ max, measured in nanometers, is determined. The color exhibited by the dye when exposed to white light is the color complementary to the color corresponding to λ max, as determined, e.g., by use of the CIE chromaticity diagram.

Tabulations of Hammett substituent constants, also called Hammett sigma parameters, can be found in *Lange's Handbook of Chemistry*, 12th ed., McGraw-Hill, (New York:1979) pp. 3-134 to 3-137, incorporated herein by reference. Additional tabulations of Hammett sigma parameters can be found in C. Hansch and A. Leo, *Substituent Constants for Correlation Analysis in Chemistry and Biology*, John Wiley and Sons, (New York:1979), incorporated herein by reference. Positive values of the Hammett sigma parameter represent electron withdrawal by the substituent group, while negative values of the Hammett sigma parameter represent electron donation by the substituent group. The values of the Hammett sigma parameters also depend upon the position of substitution. Unless otherwise stated, Hammett sigma parameters used herein will be those for substitution in the para position, denoted by $\rho_p$ in the aforementioned references. Additional tabulations of Hammett sigma parameters, as well as methods for estimating those Hammett sigma parameters not tabulated, are given in *Correlation Analysis in Chemistry*, edited by N. B. Chapman and J. Shorter, Plenum Press, (New York:1978), incorporated herein by reference.

The algebraic sum of the Hammett sigma parameters for $R^1$, $R^2$, $R^3$, and $R^4$, hereinafter denoted by the symbol $S_{1-4}$, may be defined mathematically by the formula:

$$S_{1-4} = \rho_p(R^1) + \rho_p(R^2) + \rho_p(R^3) + \rho_p(R^4)$$

wherein $\rho_p(R^i)$ is the value of the para position Hammett sigma parameter for $R^i$.

Increased values of $S_{1-4}$ result in decreased values of λmax. Values of $S_{1-4}$ of about −0.52 or greater, i.e. more positive, result in λmax occurring at wavelengths of about 575 nanometers or less. Dyes having an $S_{1-4}$ in the range of −0.52 to 0 have λmax in the range of 575 nanometers down to about 530 nanometers, and exhibit colors ranging from purplish blue to magenta, with many such dyes falling directly in the magenta region when viewed with white light. For $S_{1-4}$ values greater than 0, λmax tends to be below about 530 nanometers, thereby yielding colors tending toward red and, in one case, to yellow.

Values of $S_{1-4}$ greater than about −0.6 can be achieved by appropriate selection of the chemical structures for $R^1$, $R^2$, $R^3$, and $R^4$. More particularly, the value of $S_{1-4}$ can be increased by substitution of electron-withdrawing groups, i.e. groups having positive Hammett sigma parameters, onto one or more of $R^1$, $R^2$, $R^3$, and $R^4$, while at the same time limiting the electron-donating substituents that occur on $R^1$, $R^2$, $R^3$, and $R^4$.

Where $R^1$, $R^2$, $R^3$, or $R^4$ is an alkyl group, it is preferred that it contain 1 to 6 carbon atoms. Where $R^1$, $R^2$, $R^3$, or $R^4$ is an aryl group, it is preferred that it contain 6 to 16 carbon atoms, and that it most preferably be a phenyl or naphthyl group. Where $R^1$, $R^2$, $R^3$, or $R^4$ is an acyl group, i.e.,

it is preferred that R be an alkyl group having 1 to 10 carbon atoms, a substituted or unsubstituted phenyl group, or a substituted or unsubstituted naphthyl group. When R is a substituted naphthyl or substituted phenyl group, it is preferred that the substituents on the naphthyl or phenyl group be electron-withdrawing substituents, i.e. $\rho_p > 0$. If $R^1$, $R^2$, $R^3$, and $R^4$ is an acyl group, it is preferred that it contain 1 to 14 carbon atoms. Where $R^1$, $R^2$, $R^3$, or $R^4$ is a substituted alkyl or aryl group, the substituents are preferably electron-withdrawing. Representative examples of such suitable electron-withdrawing substituents include —Cl, —F, —Br, —CN, —NO₂, —OH,

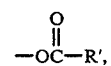

where R' is an unsubstituted alkyl group having 1 to 10 carbon atoms, a substituted alkyl group having 1 to 10 carbon atoms and preferably being substituted with one or more halogen atoms, unsubstituted aryl groups, e.g., phenyl, naphthyl, or substituted aryl groups, e.g. substituted phenyl, substituted naphthyl, wherein the substituents are preferably halogen atoms or halo-substituted alkyl groups, preferably lower alkyl (1-4 carbon atoms). Where $R^1$, $R^2$, $R^3$, or $R^4$ is an acyl group, the acyl group may contain, but is not required to contain, an electron-withdrawing substituent, since the acyl group itself is strongly electron-withdrawing. $R^1$ and $R^2$ groups or the $R^3$ and $R^4$ groups can be joined to form a five or six-membered ring structure, i.e.,

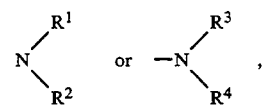

wherein the members forming the ring include nitrogen and carbon atoms, and, optionally oxygen and sulfur atoms. $R^5$ can be an unsubstituted or a substituted alkyl group, having, for example, 1 to 6 carbon atoms, an unsubstituted or substituted aryl group, having, for example, 6 to 16 carbon atoms in a monocyclic or polylcyclic configuration. Where $R^5$ is an aryl group, it is preferably a phenyl group or a naphthyl group. Representative examples of $R^5$ include the phenyl group, the ethyl group, and the p-methoxy phenyl group. When $R^5$ is a substituted alkyl or aryl group, representative substituent groups include methyl groups, ethyl groups, methoxy groups, and ethoxy groups.

Where $R^6$, $R^7$, $R^8$, $R^9$, $R^{10}$, $R^{11}$ is an alkyl or an alkoxy group, it is preferred that it contain 1 to 6 carbon atoms. Where $R^6$, $R^7$, $R^8$, $R^9$, $R^{10}$, or $R^{11}$ are substituted alkyl or substituted alkoxy groups, it is preferred that the substituents be halogens. $A^-$ represents any stable anion, preferably $Cl^-$ or $I^-$.

Representative examples of phenazine dyes of the present invention are set forth in Table I. λmax was measured in methanol, unless otherwise indicated.

TABLE I

| Dye | R$^1$ | R$^2$ | R$^3$ | R$^4$ | R$^5$ | R$^6$, R$^7$, R$^8$ | R$^9$ | R$^{10}$ | R$^{11}$ | A | λmax (nm) | S$_{1-4}$ |
|---|---|---|---|---|---|---|---|---|---|---|---|---|
| A | NCCH$_2$CH$_2$— | NCCH$_2$CH$_2$— | NCCH$_2$CH$_2$— | —C$_6$H$_5$ | H | H | H | H | Cl$^-$ | 561* | −.12 | |
| B | CF$_3$CH$_2$— | —CH$_3$ | CF$_3$CH$_2$— | —CH$_3$ | —C$_6$H$_4$CH$_3$ | H | H | H | H | Cl$^-$ | 547* | 0 |
| C | NCCH$_2$CH$_2$— | NCCH$_2$CH$_2$—H | H | —C$_6$H$_{11}$ | H | H | H | H | Cl$^-$ | 543* | −.06 |
| D | CF$_3$CH$_2$— | NCCH$_2$CH$_2$— | H | —C$_6$H$_3$Cl$_2$C(O)— | —C$_6$H$_5$ | H | H | H | H | 514* | +.66 |
| E | NCCH$_2$CH$_2$— | NCCH$_2$CH$_2$— | H | —C$_6$H$_5$C(O)— | —C$_6$H$_5$ | H | H | H | H | I$^-$ | 537, 561* | +.40 |

TABLE I-continued

| Dye | R¹ | R² | R³ | R⁴ | R⁵ | R⁶, R⁷, R⁸ | R⁹ | R¹⁰ | R¹¹ | A | λmax (nm) | $S_{1-4}$ |
|---|---|---|---|---|---|---|---|---|---|---|---|---|
| F | NCCH₂CH₂— | NCCH₂CH₂— | H | 1-naphthyl-C(=O)— | phenyl | H | H | H | H | I⁻ | 528, 544* | |
| G | NCCH₂CH₂— | NCCH₂CH₂— | H | 3,4-dichlorophenyl-C(=O)— | phenyl | H | H | H | H | I⁻ | 532* | +.49 |
| H | NCCH₂CH₂— | NCCH₂CH₂— | H | 4-CF₃-phenyl-C(=O)— | phenyl | H | H | H | H | I⁻ | 529, 544* | +.50 |
| I | NCCH₂CH₂— | NCCH₂CH₂— | H | 4-(phenyl-SO₂)-phenyl-C(=O)— | phenyl | H | H | H | H | I⁻ | 529, 544* | +.52 |
| J | NCCH₂CH₂— | NCCH₂CH₂— | H | H | 4-OCH₃-phenyl | H | —CH₃ | —CH₃ | H | I⁻ | 532 | −.06 |

TABLE I-continued
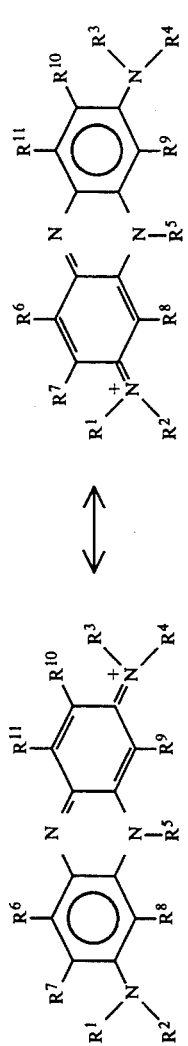
| Dye | R$^1$ | R$^2$ | R$^3$ | R$^4$ | R$^5$ | R$^6$, R$^7$, R$^8$ | R$^9$ | R$^{10}$ | R$^{11}$ | A | $\lambda$max (nm) | S$_{1-4}$ |
|---|---|---|---|---|---|---|---|---|---|---|---|---|
| K | NCCH$_2$CH$_2$— | NCCH$_2$CH$_2$— | —CH$_3$ | —CH$_3$ | ⌬—OCH$_3$ | H | H | H | H | I$^-$ | 560 | −.34 |
| L | NCCH$_2$CH$_2$— | NCCH$_2$CH$_2$— | *** | —*** | ⌬—OCH$_3$ | H | H | H | H | I$^-$ | 554 | |
| M | NCCH$_2$CH$_2$— | NCCH$_2$CH$_2$— | H | H | ⌬—OCH$_3$ | H | H | —CH$_3$ | H | I$^-$ | 534 | −.06 |
| N | NCCH$_2$CH$_2$— | NCCH$_2$CH$_2$— | H | H | ⌬—OCH$_3$ | H | H | H | —Cl | I$^-$ | 542 | −.06 |

TABLE I-continued

| Dye | R$^1$ | R$^2$ | R$^3$ | R$^4$ | R$^5$ | R$^6$, R$^7$, R$^8$ | R$^9$ | R$^{10}$ | R$^{11}$ | A | λmax (nm) | S$_{1-4}$ |
|---|---|---|---|---|---|---|---|---|---|---|---|---|
| O | NCCH$_2$CH$_2$— | NCCH$_2$CH$_2$— | —CH$_2$–C$_6$H$_5$ | —CH$_2$–C$_6$H$_5$ | –C$_6$H$_4$–OCH$_3$ | H | H | H | H | I$^-$ | 554 | −.18 |
| P | —CH$_2$CH$_3$ | —CH$_2$CH$_3$ | H | H | –C$_6$H$_4$–OCH$_3$ | H | H | —CH$_3$ | H | I$^-$ | 550 | −.26 |
| Q | —CH$_2$CH$_3$ | —CH$_2$CH$_3$ | H | H | –C$_6$H$_4$–OCH$_3$ | H | H | H | —Cl | I$^-$ | 555 | −.26 |
| R | —CH$_2$CH$_3$ | —CH$_2$CH$_3$ | H | H | –C$_6$H$_4$–OCH$_3$ | H | —CH$_3$ | —CH$_3$ | H | I$^-$ | 555 | |

TABLE I-continued $$\begin{array}{c}\text{structure with } R^1, R^2, R^3, R^4, R^5, R^6, R^7, R^8, R^9, R^{10}, R^{11} \text{ and } A^-\end{array} \leftrightarrow \begin{array}{c}\text{resonance structure}\end{array}$$

| Dye | $R^1$ | $R^2$ | $R^3$ | $R^4$ | $R^5$ | $R^6, R^7, R^8$ | $R^9$ | $R^{10}$ | $R^{11}$ | A | λmax (nm) | $S_{1-4}$ |
|---|---|---|---|---|---|---|---|---|---|---|---|---|
| S | —CH$_2$CH$_3$ | —CH$_2$CH$_3$ | H | H | 4-OCH$_3$-phenyl | H | H | H | H | I$^-$ | 549 | |
| T | —CH$_2$CH$_3$ | —CH$_2$CH$_3$ | H | H | 4-OCH$_3$-phenyl | H | H | Cl | H | I$^-$ | 556 | |
| U | —CH$_2$CH$_3$ | —CH$_2$CH$_3$ | H | —CH$_2$CH$_3$ | 4-OCH$_3$-phenyl | H | H | H | H | I$^-$ | 557 | −.39 |
| V | —CH$_2$CH$_3$ | —CH$_2$CH$_3$ | CH$_3$ | —CH$_3$ | 4-OCH$_3$-phenyl | H | H | H | H | I$^-$ | 570 | −.54 |

TABLE I-continued

| Dye | $R^1$ | $R^2$ | $R^3$ | $R^4$ | $R^5$ | $R^6, R^7, R^8$ | $R^9$ | $R^{10}$ | $R^{11}$ | A | λmax (nm) | $S_{1-4}$ |
|---|---|---|---|---|---|---|---|---|---|---|---|---|
| W | —CH$_2$CH$_3$ | —CH$_2$CH$_3$ | CH$_2$CH$_3$ | —CH$_2$CH$_3$ | 4-methoxyphenyl | H | H | H | H | I$^-$ | 570 | −.54 |
| X | —CH$_2$CH$_3$ | —CH$_2$CH$_3$ | —CH$_2$CH$_3$ | —CH$_2$CH$_3$ | 3-methylphenyl | H | H | H | H | I$^-$ | 573 | |
| Y | —CH$_2$CH$_3$ | —CH$_2$CH$_3$ | —CH$_2$CH$_3$ | —CH$_2$CH$_3$ | phenyl | H | —CH$_3$ | H | H | I$^-$ | 574 | |
| Z | —CH$_2$CH$_3$ | —CH$_2$CH$_3$ | *** | *** | 4-methoxyphenyl | H | —CH$_3$ | H | H | I$^-$ | 570 | |
| AA | —CH$_2$CH$_3$ | —CH$_2$CH$_3$ | —CH—CH$_2$CH$_2$— | —CH$_3$ | 4-methoxyphenyl | H | —CH$_3$ | **** | H | I$^-$ | 572 | |

TABLE I-continued

| Dye | $R^1$ | $R^2$ | $R^3$ | $R^4$ | $R^5$ | $R^6, R^7, R^8$ | $R^9$ | $R^{10}$ | $R^{11}$ | A | $\lambda_{max}$ (nm) | $S_{1-4}$ |
|---|---|---|---|---|---|---|---|---|---|---|---|---|
| BB | —CH$_2$CH$_3$ | —CH$_2$CH$_3$ | —CH$_2$CH$_2$— | —CH$_3$ | 4-methoxyphenyl | H | —CH$_3$ | **** | H | I$^-$ | 522 | |
| CC | —CH$_3$ | —CH$_3$ | —CH$_3$ | —CH$_3$ | 4-methoxyphenyl | H | H | H | H | I$^-$ | 567 | |
| DD | —CH$_3$ | —CH$_3$ | —CH$_3$ | —CH$_3$ | 4-nitrophenyl | H | H | H | H | I$^-$ | 564 | −.56 |
| EE | —CH$_3$ | —CH$_3$ | —CH$_3$ | —CH$_3$ | 4-methoxyphenyl | H | H | H | H | I$^-$ | 568 | |
| FF | —CH$_3$ | —CH$_3$ | —CH$_3$ | —CH$_3$ | phenyl | H | H | H | H | I$^-$ | 568 | |

TABLE I-continued
| Dye | R¹ | R² | R³ | R⁴ | R⁵ | R⁶, R⁷, R⁸ | R⁹ | R¹⁰ | R¹¹ | A | λmax (nm) | $S_{1-4}$ |
|---|---|---|---|---|---|---|---|---|---|---|---|---|
| GG | —CH₃ | —CH₃ | —CH₃ | —CH₃ | 4-Cl-C₆H₄ | H | H | H | H | I⁻ | 568 | |
| HH | —CH₃ | —CH₃ | —CH₃ | —CH₃ | 3-CH₃-C₆H₄ | H | H | H | H | I⁻ | 567 | |
| II | —CH₃ | —CH₃ | —CH₃ | —CH₃ | 2-CH₃-C₆H₄ | H | H | H | H | I⁻ | 570 | |
| JJ | —CH₃ | —CH₃ | —CH₂CH₂CN | —CH₂CH₂CN | 4-OCH₃-C₆H₄ | H | H | H | H | I⁻ | 560 | −.34 |

TABLE I-continued

| Dye | R$^1$ | R$^2$ | R$^3$ | R$^4$ | R$^5$ | R$^6$, R$^7$, R$^8$ | R$^9$ | R$^{10}$ | R$^{11}$ | A | λmax (nm) | S$_{1-4}$ |
|---|---|---|---|---|---|---|---|---|---|---|---|---|
| KK | —CH$_3$ | —CH$_3$ | —CH$_2$CH$_2$CN | —CH$_2$CH$_2$CN | naphthyl | H | H | H | H | I$^-$ | 560 | −.34 |
| LL | —CH$_3$ | —CH$_3$ | —CH$_3$ | —CH$_3$ | 4-methoxyphenyl | H | H | —CH$_2$CH$_2$CH$_2$— | | I$^-$ | 571 | −.56 |
| MM | —CH$_3$ | —CH$_3$ | H | H | 4-methoxyphenyl | H | H | —CH$_2$—CH$_2$—CH$_2$— | | I$^-$ | 544 | −.28 |
| NN | —CH$_3$ | —CH$_3$ | H | H | 4-methoxyphenyl | H | H | H | H | I$^-$ | 552 | −.28 |

TABLE I-continued

| Dye | R¹ | R² | R³ | R⁴ | R⁵ | R⁶, R⁷, R⁸ | R⁹ | R¹⁰ | R¹¹ | A | λmax (nm) | S₁₋₄ |
|---|---|---|---|---|---|---|---|---|---|---|---|---|
| OO | —CH₃ | —CH₃ | —CH₃ | —CH₃ | —C₆H₄—OCH₃ | H | H | —CH₂CH₂CH₂— | | I⁻ | 568 | —.44 |
| PP | —CH₃ | —CH₃ | —CH₂CH₂OH | —CH₂CH₂OH | —C₆H₄—OCH₃ | H | H | H | H | I⁻ | 569 | |
| QQ | —CH₃ | —CH₃ | —CH₂CH₂O—CO—C₆H₄—CF₃ | —CH₂CH₂O—CO—C₆H₄—CF₃ | —C₆H₄—OCH₃ | H | H | H | H | I⁻ | 564 | |
| RR | —CH₃ | —CH₃ | —CH₂CH₂O—CO—CF₃ | —CH₂CH₂O—CO—CF₃ | —C₆H₄—OCH₃ | H | H | H | H | I⁻ | ** | |

TABLE I-continued

| Dye | R¹ | R² | R³ | R⁴ | R⁵ | R⁶, R⁷, R⁸ | R⁹ | R¹⁰ | R¹¹ | A | λmax (nm) | $S_{1-4}$ |
|---|---|---|---|---|---|---|---|---|---|---|---|---|
| SS | —CH₃ | —CH₃ | —CH₂CH₂OH | —CH₃ | 4-CH₃OC₆H₄— | H | H | H | H | I⁻ | 567 | −.51 |
| TT | —CH₃ | —CH₃ | —CH₂COOH | —CH₂COOH | 4-CH₃OC₆H₄— | H | H | H | H | I⁻ | 547 | −.42 |
| UU | —CH₂CH₂CN | —CH₂CH₂CN | H | H | 4-CH₃OC₆H₄— | H | H | —CH₃ | H | I⁻ | 534 | −.06 |
| VV | —CH₂CH₂CN | —CH₂CH₂CN | H | H | 4-CH₃OC₆H₄— | H | H | —CH₃ | CH₃ | I⁻ | 532 | −.06 |

TABLE I-continued

| Dye | $R^1$ | $R^2$ | $R^3$ | $R^4$ | $R^5$ | $R^6, R^7, R^8$ | $R^9$ | $R^{10}$ | $R^{11}$ | A | $\lambda_{max}$ (nm) | $S_{1-4}$ |
|---|---|---|---|---|---|---|---|---|---|---|---|---|
| WW | —CH$_2$CH$_2$CN | —CH$_2$CH$_2$CN | H | H | 4-methoxyphenyl | H | H | H | Cl | I$^-$ | 542 | −.06 |
| XX | —CH$_2$CH$_2$CN | —CH$_2$CH$_2$CN | H | H | 4-methoxyphenyl | H | H | H | H | I$^-$ | 533 | −.06 |
| YY | —CH$_2$CH$_2$CN | —CH$_2$CH$_2$CN | —CH$_2$CH$_3$ | H | 4-methoxyphenyl | H | H | H | H | I$^-$ | 539 | −.19 |
| ZZ | —CH$_2$CH$_2$CN | —CH$_2$CH$_2$CN | —C(O)-(4-trifluoromethylphenyl) | H | 4-methoxyphenyl | H | H | H | H | I$^-$ | 523, 454 | +.50 |

TABLE I-continued
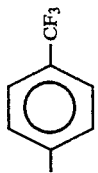
| Dye | R¹ | R² | R³ | R⁴ | R⁵ | R⁶, R⁷, R⁸ | R⁹ | R¹⁰ | R¹¹ | A | λmax (nm) | $S_{1-4}$ |
|---|---|---|---|---|---|---|---|---|---|---|---|---|
| AAA | —CH₂CH₂CN | —CH₂CH₂CN | 4-CF₃-C₆H₄-C(O)— | H | 4-OCH₃-C₆H₄— | H | H | —CH₃ | H | I⁻ | 544, 446 | +.50 |
| BBB | —CH₂CH₂CN | —CH₂CH₂CN | 4-CF₃-C₆H₄-C(O)— | H | 4-OCH₃-C₆H₄— | H | H | —CH₃ | —CH₃ | I⁻ | 566, 429 | +.50 |
| CCC | —CH₂CH₂CN | —CH₂CH₂CN | 1-naphthyl-C(O)— | H | 4-OCH₃-C₆H₄— | H | H | H | H | I⁻ | 519-458 | |
| DDD | —CH₂CH₂CN | —CH₂CH₂CN | 1-naphthyl-C(O)— | H | 4-OCH₃-C₆H₄— | H | H | —CH₃ | H | I⁻ | 543, 452 | |

TABLE I-continued

| Dye | $R^1$ | $R^2$ | $R^3$ | $R^4$ | $R^5$ | $R^6, R^7, R^8$ | $R^9$ | $R^{10}$ | $R^{11}$ | A | λmax (nm) $S_{1-4}$ |
|---|---|---|---|---|---|---|---|---|---|---|---|
| EEE | —CH$_2$CH$_2$CN | —CH$_2$CH$_2$CN | —CH$_2$CH$_2$CH$_2$— | —CH$_3$ | p-C$_6$H$_4$OCH$_3$ | H | H | **** | H | I$^-$ | 559 |
| FFF | —CH$_2$CH$_2$CN | —CH$_2$CH$_2$CN | —CH$_2$CH$_2$— | —CH$_3$ | p-C$_6$H$_4$OCH$_3$ | H | H | **** | H | I$^-$ | 514 |
| GGG | —CH$_2$CH$_2$CN | —CH$_2$CH$_2$CN | —CH$_2$CH$_2$CH$_2$— | —CH$_2$CH$_2$CN | p-C$_6$H$_4$OCH$_3$ | H | H | **** | H | I$^-$ | 553 |
| HHH | —CH$_2$CH$_2$CN | —CH$_2$CH$_2$CN | *** | *** | p-C$_6$H$_4$OCH$_3$ | H | H | H | H | I$^-$ | 554 |

TABLE I-continued

| Dye | R¹ | R² | R³ | R⁴ | R⁵ | R⁶, R⁷, R⁸ | R⁹ | R¹⁰ | R¹¹ | A | λmax (nm) | $S_{1-4}$ |
|---|---|---|---|---|---|---|---|---|---|---|---|---|
| III | —CH₂CH₂CN | CH₂CH₂CN | —C₆H₅CH₂— | —C₆H₅CH₂— | —C₆H₄—OCH₃ | H | H | H | H | I⁻ | 554 | +.06 |
| JJJ | —CH₂CH₂CN | —CH₂CH₂CN | —CH₂CH₂NCH₂CH₂— C(=O)—C₆H₄—CF₃ | —CH₂CH₂NCH₂CH₂— C(=O)—C₆H₄—CF₃ | —C₆H₄—OCH₃ | H | H | H | H | I⁻ | 555 | |
| KKK | —CH₂CH₂CN | —CH₂CH₂CN | —CH₂CH₂OH | —CH₂CH₂OH | —C₆H₄—OCH₃ | H | H | H | H | I⁻ | 562 | −.24 |
| LLL | —CH₂CH₂CN | CH₂CH₂CN | —CH₂CH₂—O—C(=O)—C₆H₄—CF₃ | —CH₂CH₂—O—C(=O)—C₆H₄—CF₃ | —C₆H₄—OCH₃ | H | H | H | H | I⁻ | 554 | |

TABLE I-continued

| Dye | $R^1$ | $R^2$ | $R^3$ | $R^4$ | $R^5$ | $R^6, R^7, R^8$ | $R^9$ | $R^{10}$ | $R^{11}$ | A | λmax (nm)** | $S_{1-4}$ |
|---|---|---|---|---|---|---|---|---|---|---|---|---|
| MMM | —CH$_2$CH$_2$CN | —CH$_2$CH$_2$CN | —CH$_2$CH$_2$O—C(=O)—CF$_3$ | —CH$_2$CH$_2$O—C(=O)—CF$_3$ | —C$_6$H$_4$—OCH$_3$ | H | H | H | H | I$^-$ | 547** | −.29 |
| NNN | —CH$_2$CH$_2$CN | —CH$_2$CH$_2$CN | —CH$_2$CH$_2$OH | —CH$_3$ | —C$_6$H$_4$—OCH$_3$ | H | H | H | H | I$^-$ | 560 | |
| OOO | —CH$_2$CH$_2$CN | —CH$_2$CH$_2$CN | —CH$_2$CH$_2$O—C(=O)—C$_6$H$_4$—CF$_3$ | —CH$_3$ | —C$_6$H$_4$—OCH$_3$ | H | H | H | H | I$^-$ | 556 | |
| PPP | —CH$_2$CH$_2$CN | —CH$_2$CH$_2$CN | —CH$_2$CH$_2$O—C(=O)—C$_6$H$_3$(NO$_2$)$_2$ | —CH$_2$CH$_2$O—C(=O)—C$_6$H$_3$(NO$_2$)$_2$ | —C$_6$H$_4$—OCH$_3$ | H | H | H | H | I$^-$ | 554 | |

TABLE I-continued

| Dye | R¹ | R² | R³ | R⁴ | R⁵ | R⁶,R⁷,R⁸ | R⁹ | R¹⁰ | R¹¹ | A | λmax (nm) | S₁₋₄ |
|---|---|---|---|---|---|---|---|---|---|---|---|---|
| QQQ | —CH₂CH₂CN | —CH₂CH₂CN | —CH₂CH₂O₂C-(2,4-dinitrophenyl) | —CH₃ | 4-CH₃O-phenyl | H | H | H | H | I⁻ | 557 | |
| RRR | —CH₂CH₂CN | —CH₂CH₂CN | —CH₂CH₂O—C(=O)—C(CH₃)=CH₂ | —CH₂CH₂O—C(=O)—C(CH₃)=CH₂ | 4-CH₃O-phenyl | H | H | H | H | I⁻ | 553 | |
| SSS | —CH₂CH₂CN | —CH₂CH₂CN | —CH₂CH₂O—C(=O)—CH₃ | —CH₂CH₂O—C(=O)—CH₃ | 4-CH₃O-phenyl | H | H | H | H | I⁻ | 554 | |
| TTT | —CH₂CH₂CN | —CH₂CH₂CN | —CH₂CH₂O—C(=O)—C(CH₃)=CH₂ | —CH₃ | 4-CH₃O-phenyl | H | H | H | H | I⁻ | 556 | |

TABLE I-continued
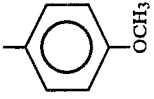
| Dye | R¹ | R² | R³ | R⁴ | R⁵ | R⁶, R⁷, R⁸ | R⁹ | R¹⁰ | R¹¹ | A | λmax (nm) | $S_{1-4}$ |
|---|---|---|---|---|---|---|---|---|---|---|---|---|
| UUU | —CH₂CH₂CN | —CH₂CH₂CN | —CH₂COOH | —CH₂COOH | 4-methoxyphenyl | H | H | H | H | I⁻ | 534 | |
| VVV | —CH₂CH₂CN | —CH₂CH₂CN | —CH₂COOH | —CH₂COOH | 4-methoxyphenyl | H | H | H | H | I⁻ | 544 | |
| WWW | —CH₂CH₂OC(O)CH₃ | H | phenyl | H | phenyl | H, —CH₃, H | H | —CH₃ | H | I⁻ | 482 | +.51 |
| XXX | 1-naphthoyl | H | 1-naphthoyl | H | phenyl | H, —CH₃, H | H | —CH₃ | H | I⁻ | 475 | |

TABLE I-continued

| Dye | R$^1$ | R$^2$ | R$^3$ | R$^4$ | R$^5$ | R$^6$, R$^7$, R$^8$ | R$^9$ | R$^{10}$ | R$^{11}$ | A | λmax (nm) | S$_{1-4}$ |
|---|---|---|---|---|---|---|---|---|---|---|---|---|
| YYY | 2-naphthoyl | H | 2-naphthoyl | H | phenyl | H, —CH$_3$ | H | —CH$_3$ | H | I$^-$ | 475 | |

*measured in saran polymeric binder
**measured in CH$_2$Cl$_2$

***R$^3$ and R$^4$ with N form the ring =N

****R$^3$ and R$^{10}$ with N and two carbon atoms from the phenyl ring form a ring
R$^{10}$ and R$^{11}$ with two carbon atoms from the phenyl ring form a ring
R$^3$ and R$^4$ with =N form a ring The dyes of the present invention can be colorless when they are in the leuco form, and they can exhibit a yellow to orange hue ($\lambda$max in the range of about 435 to about 490 nanometers), a red hue ($\lambda$max in the range of about 490 to about 530 nanometers), or a reddish magenta to violet hue ($\lambda$max in the range of about 530 to about 560 nanometers), when in their oxidized form. While in their colored form, they exhibit excellent resistance to fading or degradation.

The dyes of this invention can be prepared by the process described below. A phenylene diamine derivative, e.g., N,N-diethyl-p-phenylene diamine, an aniline derivative having no para substituent, e.g., N,N-diethylaniline, and an acid, e.g., HCl, are combined in a solvent, preferably water, in a reaction vessel and stirred, preferably at or below room temperature (25° C.). An oxidizing agent, preferably sodium dichromate, is added to the solution to couple the phenylene diamine derivative and the aniline derivative. Any aniline derivative containing an unsubstituted —$NH_2$ group or alkylamine compound containing an unsubstituted —$NH_2$ group is then added to the mixture. The resulting mixture is then stirred and optionally heated over a sufficient period of time to bring about formation of the dye product. To the resulting solution is added a salt, preferably an ionizable halide salt, e.g., KI, NaCl, to precipitate the dye product. The solution is then cooled, and the dye collected by filtration and dried in air.

The dyes of the present invention can be used to prepare leuco dyes that are useful in thermographic and photothermographic imaging systems. They are particularly useful for preparing leuco dyes to be used in the preparation of transparencies for overhead projection because the dyes can exhibit long shelf-life in the unoxidized, colorless state and further exhibit excellent heat and light stability in the oxidized, colored state.

The leuco forms of the dyes of this invention can be prepared in the following manner. The dye of the present invention is dissolved in water, methylene chloride is added, and the pH is adjusted to about 10. In an inert atmosphere, the dye is reduced with sodium dithionite. Acylation can be effected by adding an appropriate acid chloride. When the reaction is complete, the methylene chloride layer is isolated and treated with a decolorizing agent, e.g., Attapulgus clay. Removal of solvent yields the leuco form of the dye.

The following non-limiting examples will further illustrate the invention.

EXAMPLE 1

Synthesis of 3 amino-5-phenyl-7-bis (2 cyanoethyl)amino phenazinium chloride (Dye C of Table I)

A 3-liter round-bottomed flask fitted with a mechanical stirrer was loaded with 16.6 g (0.066 mole) of 4-(bis-(2-cyanoethyl)amino) aniline in 800 ml of distilled water. A 10% excess of aniline (13.56 g, 0.1456 mole) and 200 ml of distilled water were added to the mixture. The mixture was cooled to 0° C. in an ice bath, and 10 g concentrated hydrochloric acid in 25 ml of water were added. Then 6.31 g (0.0883 mole) of sodium dichromate in 25 ml of water was added. The temperature rose to 7° C. Stirring was continued as 9 ml of concentrated hydrochloric acid in 25 ml of distilled water was added over a period of two hours. After 16 hours the temperature had risen to 20° C. The mixture was heated under reflux for 4 hours and then filtered hot. The filter cake was washed with 1.5 liters of boiling water. The combined filtrates were concentrated to 1.4 liters and then heated to 75° C. as 200 g of sodium chloride were added.

The mixture was cooled to room temperature, chilled in an ice bath, and the solid was then recovered by filtration to give 14.651 g (yield=51.6%). ($\lambda$max=537 nm in methanol).

EXAMPLE 2

Synthesis of 3-amino-7-bis(2-cyanoethyl)amino-2,4-dimethyl-5 p-methoxyphenylphenaziniumiodide (Dye J of Table I)

An Erlenmeyer flask was loaded with 1.0 g (0.004 mole) of N,N-bis(2-cyanoethyl)-p-phenylene diamine hydrochloride, 1.0 g concentrated hydrochloric acid, 0.5 g (0.004 mole) 2,5-dimethylaniline, and 100 ml methanol. As the resulting mixture was being stirred at room temperature, 0.8 g (0.0027 mole) of sodium dichromate dihydrate ($Na_2Cr_2O_7.2H_2O$) in 3 g $H_2O$ was added dropwise. After two minutes, 0.5 g (0.004 mole) of p-anisidine in 3 g methanol was added. After about 20 minutes, an additional 0.5 g (0.0017 mole) of $Na_2Cr_2O_7.2H_2O$ in 2 g $H_2O$ was added. After the mixture was stirred for about 1 hour, the solution, which was dark red in color, was reduced in volume and 50 ml of water was added. The solution was heated, and the liquid decanted. Water (50 ml) was added to the residue, and this solution was heated, and the water decanted. The combined aqueous solutions were treated with diatomaceous earth (Celite ®) and filtered hot. To the hot solution was added 5.0 g of potassium iodide to precipitate the dye in the form of a salt. The solution was cooled, the dye recovered by filtration, and dried in air. The yield was 1.8 g (78%). The wave lengths were as follows:

$\lambda$max=533 nm in $H_2O$
$\lambda$max=532 nm in $CH_3OH$
$\lambda$max=529 nm in $CH_2Cl_2$

EXAMPLE 3

Preparation of 3-(4-(phenylsulfonyl)benzamido)5-phenyl-7-bis(2 cyanoethyl)amino-5,10-dihydro-10(4-(phenylsulfonyl) benzoyl) phenazine from Dye C (Table I)

This example demonstrates preparation of a leuco dye suitable for use in a thermally imageable composition.

A 1-liter 3-necked flask was fitted with a Claisen head with two dropping funnels, a mechanical stirrer, and a pH electrode. A solution containing 5.0 g (0.012 mole) of the dye prepared in Example 1, 210 ml of water and 0.2 g of ethylene diamine tetraacetic acid was added to the flask and stirred, while 256 ml of methylene chloride was added. The system was closed and flushed with argon, the pH adjusted to 10, then 2.44 g (0.014 mole) of sodium dithionite was added. The solution turned orange and the pH dropped to 3.7. Aqueous sodium hydroxide solution (25%) was added to bring the pH to 4.5, and then 7.53 g (0.027 mole) of 4-phenyl sulfonyl benzoyl chloride in 60 ml of methylene chloride was added dropwise. The pH was maintained between 4 and 5. After 1½ hours the pH was raised to 10-11. After an additional 50 minutes, the methylene chloride layer was removed and dried over calcium sulfate. The solution was treated twice with 10 g of Attapulgus clay and filtered. The solvent was then evaporated, leaving 8.14 g of solid (79% yield).

The thus-prepared leuco dye was tested in the following formulation:
- 0.19 g leuco dye
- 0.75 g (1%) phenidone in tetrahydrofuran
- 0.13 g (5%) catechol in ethanol
- 0.075 g phthalic acid
- 3.0 g tetrahydrofuran
- 0.13 g Ni(NO$_3$)$_2$
- 0.25 g phenol
- 8.0 g 15% polyvinylidene chloride (Saran ® 220) in methyl ethyl ketone The solution was coated at 3 mils (75 μm) on 4 mil (100 μm) polyester film and dried at 160° F. for 2 minutes. The dried film was imaged at a rate of 1.7 inches per second on a 3M Model 45 infrared transparency film machine. Image stability was tested on the stage of a 3M Model 66 projector. The temperature on the stage was 63° C. The results are shown in TABLE II.

TABLE II

| | Time on stage of model 66 Projector Optical Density | | | | | | | |
|---|---|---|---|---|---|---|---|---|
| | 0 hour | | 3 hours | | 6 hours | | 14 hours | |
| Filter | image | back-ground | image | back-ground | image | back-ground | image | back-ground |
| yellow | .49 | .07 | .46 | .08 | .47 | .09 | .47 | .10 |
| red | .11 | .04 | .10 | .04 | .10 | .05 | .10 | .05 |
| green | .85 | .07 | .81 | .08 | .82 | .09 | .82 | .11 |
| blue | .53 | .09 | .53 | .09 | .53 | .09 | .54 | .10 |

The high optical density readings of the image with the green and blue filters show that red is the predominant hue of the dye. The λmax is 540 nm as compared with λmax of 587 nm of Heliotrope B. The retention of these density readings after 14 hours on the stage of the projector attest to the light and heat stability of the dye; the retention of the low optical density readings of the background attest to stability of the leuco compound which is the dye precursor.

EXAMPLE 4

Synthesis of 3,7-di(N-methyl,N-2,2,2-trifluoroethyl)-amino-5-(4-methylphenyl) phenazinium chloride (Dye B of Table I)

Into a 1-liter 3-necked flask equipped with a stirrer was added p-(N-methyl-N-2,2,2-trifluoroethyl)-amino aniline (1.40 g, 0.0058 M):and N-methyl-N-2,2,2-trifluoroethyl aniline (0.764 g, 0.0041 M) with 250 ml of deionized water. The mixture was stirred vigorously as 1.55 g of concentrated hydrochloric acid in 10 ml of water was added. After 10 minutes, 2.31 g of sodium dichromate (0.0078 M) in 20 ml of water was added over a period of several minutes. After 5 minutes, p-toluidine was added (0.624 g, 0.0058 M); over the next 45 minutes, 1.2 g of concentrated hydrochloric acid was added. The solution was warmed to 42° C. and stirred overnight at this temperature. After being heated to reflux temperature for 22.5 hours, the mixture was filtered hot, and the filter cake washed with hot water. The aqueous filtrate was concentrated from 650 ml to 275 ml in a rotary vacuum dryer.

The procedure for the reduction was that described in Example 2, using p-phenylsulfonylbenzoyl chloride as the acylating agent. The λmax of the oxidized dye was 547.7 nm; its color was perceptibly more red than that of Heliotrope B(μmax=587 nm).

The leuco dye was evaluated in a formulation identical to that of Example 3 except for the use of a different dye. The procedure for evaluation was the same as that employed in Example 3. The film exhibited imaging characteristics as shown in the following table.

TABLE III

| | Optical Density | |
|---|---|---|
| Filter | Image | Background |
| yellow | .38 | .04 |
| red | .08 | .03 |
| green | 1.10 | .05 |
| blue | .48 | .07 |

From the foregoing table, it can be seen that the dye in the oxidized form is red in color.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A 3,7-diamino phenazine dye represented by the resonant structures:

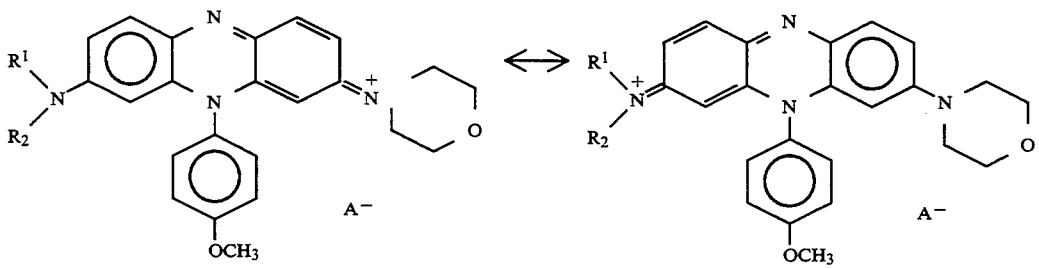

wherein R$^1$ represents ethyl or cyanoethyl, R$^2$ represents ethyl or cyanoethyl, and A$^-$ represents any stable anion.

2. A 3,7-diamino phenazine dye represented by the resonant structures

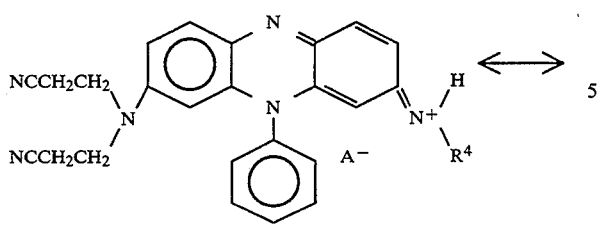

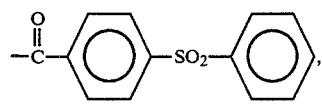

and A⁻ represents any stable anion.

3. A 3,7-diamino phenazine dye represented by the resonant structures

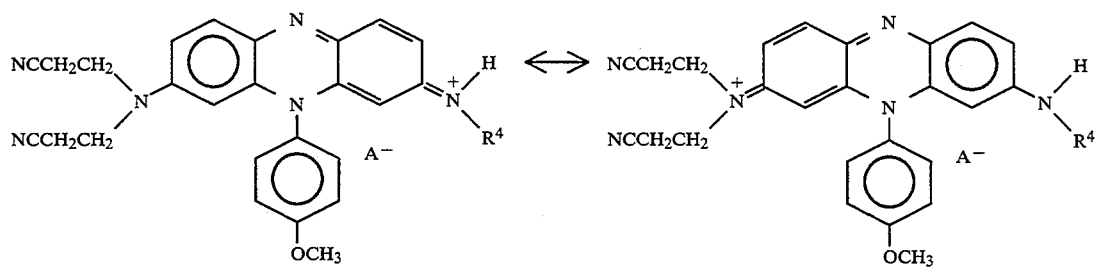

wherein $R^4$ is selected from the group consisting of

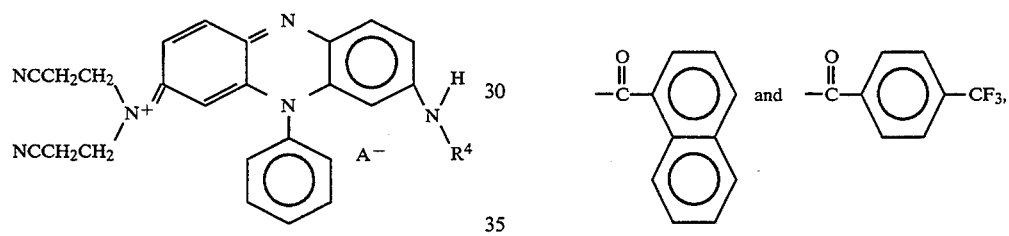

wherein $R^4$ is selected from the group consisting of

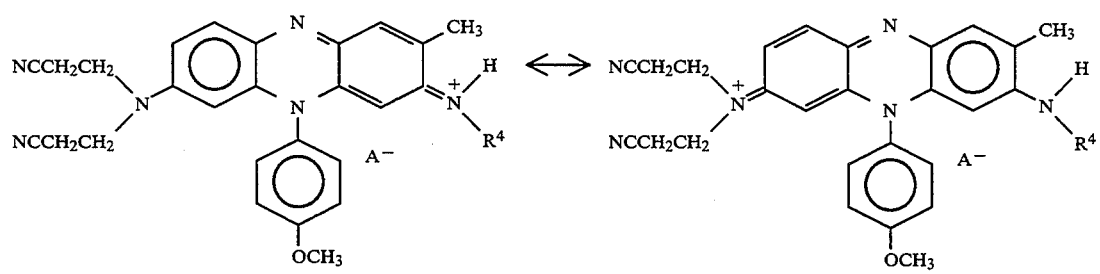

and A⁻ represents any stable anion.

4. A 3,7-diamino phenazine dye represented by the resonant structures wherein $R^4$ is selected from the group consisting of

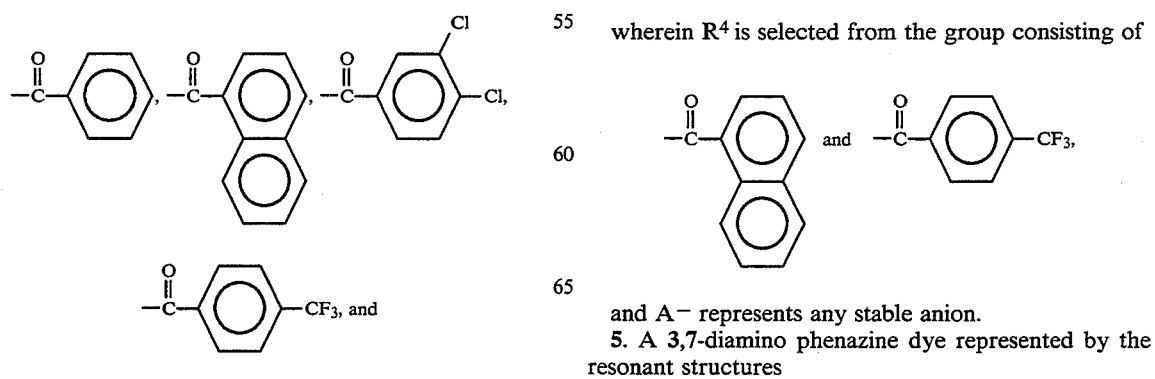

and A⁻ represents any stable anion.

5. A 3,7-diamino phenazine dye represented by the resonant structures

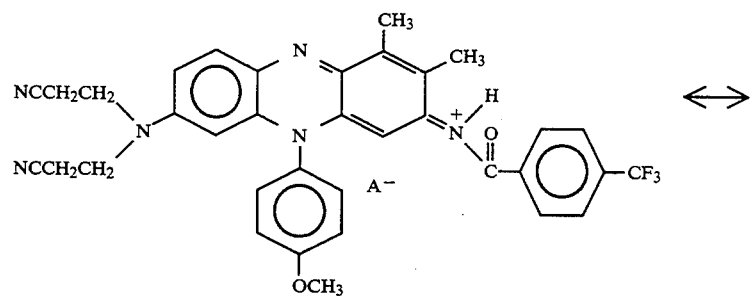
⇌
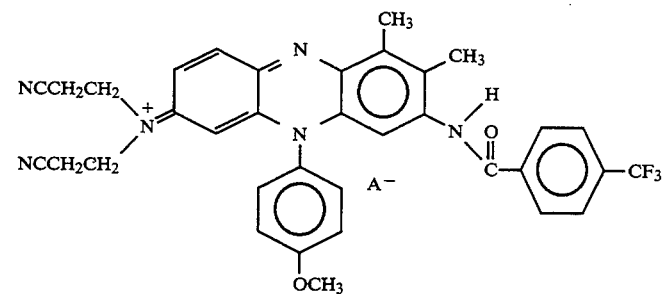
wherein A⁻ represents any stable anion.